(12) United States Patent
Hall et al.

(10) Patent No.: US 10,603,140 B2
(45) Date of Patent: Mar. 31, 2020

(54) DENTAL IMPLANT

(71) Applicant: NOBEL BIOCARE SERVICES AG, Kloten (CH)

(72) Inventors: Jan Hall, Göteborg (SE); Fredrik Kullberg, Lycke (SE)

(73) Assignee: Nobel Biocare Services AG, Kloten (CH)

( * ) Notice: Subject to any disclaimer, the term of this patent is extended or adjusted under 35 U.S.C. 154(b) by 59 days.

(21) Appl. No.: 15/123,542

(22) PCT Filed: Mar. 5, 2015

(86) PCT No.: PCT/EP2015/054570
§ 371 (c)(1),
(2) Date: Sep. 2, 2016

(87) PCT Pub. No.: WO2015/132323
PCT Pub. Date: Sep. 11, 2015

(65) Prior Publication Data
US 2017/0065377 A1 Mar. 9, 2017

(30) Foreign Application Priority Data
Mar. 7, 2014 (GB) .................................. 1404049.7

(51) Int. Cl.
*A61C 8/02* (2006.01)
*A61C 8/00* (2006.01)
(52) U.S. Cl.
CPC ............ *A61C 8/0006* (2013.01); *A61C 8/008* (2013.01); *A61C 8/0022* (2013.01); *A61C 8/0025* (2013.01); *A61C 8/0078* (2013.01)
(58) Field of Classification Search
CPC ... A61C 8/0006; A61C 8/0022; A61C 8/0025; A61C 8/0078; A61C 8/008
See application file for complete search history.

(56) References Cited

U.S. PATENT DOCUMENTS 4,697,969 A 10/1987 Sparkes
4,871,313 A 10/1989 Maillefer
(Continued)

FOREIGN PATENT DOCUMENTS

CN 101262831 A 9/2008
CN 102697570 A 10/2012
(Continued)

OTHER PUBLICATIONS

International Search Report for Application No. PCT/EP2015/054570 dated Jun. 8, 2016 in 4 pages [the ISR for the PCT Application of this US national phase application].

*Primary Examiner* — Heidi M Eide
(74) *Attorney, Agent, or Firm* — Knobbe Martens Olson & Bear LLP

(57) ABSTRACT

It is disclosed a dental implant (130; 230; 330) for promoting hone growth. The dental implant includes an elongated implant body having a coronal end portion (131; 231; 331) and an apical end portion (132; 232; 332), at least one external thread (140; 240; 340) and a flute arrangement having a depth. The flute arrangement has at least two helical flutes (150; 250; 350) that spiral in the general direction of said at least one external thread (140; 240; 340). The flutes (150; 250; 350) propagate with a greater lead than said at least one thread (140; 240 340). The flute arrangement is capable of scraping off and transferring bone debris in the coronal direction of the implant during insertion. It is also disclosed a method of using the dental implant and an implant system according to the present invention.

16 Claims, 5 Drawing Sheets

(56) References Cited

U.S. PATENT DOCUMENTS

| | | |
|---|---|---|
| 5,601,429 A | 2/1997 | Blacklock |
| 5,628,630 A | 5/1997 | Misch |
| 5,667,348 A | 9/1997 | Chen et al. |
| 5,772,374 A | 6/1998 | Ide et al. |
| 5,897,319 A | 4/1999 | Wagner et al. |
| 5,902,109 A | 5/1999 | Reams et al. |
| 6,135,772 A * | 10/2000 | Jones ............... A61C 8/00 433/174 |
| 6,273,722 B1 | 8/2001 | Phillips |
| 6,312,472 B1 | 11/2001 | Hall et al. |
| 6,382,976 B1 | 5/2002 | Wagner |
| 6,402,515 B1 | 6/2002 | Palti et al. |
| 6,419,708 B1 | 6/2002 | Hall et al. |
| 6,450,748 B1 | 9/2002 | Hsu |
| 6,604,945 B1 | 8/2003 | Jones |
| 6,679,701 B1 | 1/2004 | Blacklock |
| 6,730,129 B1 | 5/2004 | Hall |
| 6,918,766 B1 | 7/2005 | Hall et al. |
| 7,008,226 B2 | 3/2006 | Mayer et al. |
| 7,048,541 B2 | 5/2006 | Hall et al. |
| 7,281,925 B2 | 10/2007 | Hall |
| 7,491,058 B2 | 2/2009 | Jorneus |
| 7,597,557 B2 | 10/2009 | Fromovich et al. |
| 7,699,881 B2 | 4/2010 | Willmann |
| 7,708,558 B1 | 5/2010 | Hall et al. |
| 7,713,292 B2 | 5/2010 | Biedermann et al. |
| 7,713,307 B1 | 5/2010 | Hall et al. |
| 7,806,693 B2 | 10/2010 | Hurson |
| 8,016,593 B2 | 9/2011 | Hall |
| 8,038,442 B2 | 10/2011 | Hurson |
| 8,100,985 B2 | 1/2012 | Hall |
| 8,113,834 B2 | 2/2012 | Hall |
| 8,152,856 B2 | 4/2012 | Hall et al. |
| 8,167,618 B2 | 5/2012 | Hall |
| 8,349,009 B2 | 1/2013 | Hall et al. |
| 8,439,919 B2 | 5/2013 | Hall |
| 8,657,601 B2 | 2/2014 | Hall |
| 8,764,443 B2 | 7/2014 | Hall |
| 8,771,361 B2 | 7/2014 | Hall |
| 8,827,703 B2 | 9/2014 | Hall |
| 2002/0182567 A1 | 12/2002 | Hurson |
| 2003/0228556 A1 | 12/2003 | Miller |
| 2004/0121289 A1 | 6/2004 | Miller |
| 2005/0221258 A1 | 10/2005 | Hall |
| 2007/0083168 A1* | 4/2007 | Whiting ............... A61M 25/007 604/264 |
| 2008/0032264 A1 | 2/2008 | Hall |
| 2008/0227057 A1* | 9/2008 | Anitua Aldecoa ... A61C 8/0001 433/174 |
| 2008/0261175 A1* | 10/2008 | Hurson ............... A61C 8/0022 433/173 |
| 2009/0258328 A1 | 10/2009 | Chen |
| 2010/0009316 A1 | 1/2010 | Hurson |
| 2010/0055643 A1 | 3/2010 | Hung |
| 2010/0112519 A1 | 5/2010 | Hall et al. |
| 2010/0190138 A1 | 7/2010 | Giorno |
| 2011/0033826 A1 | 2/2011 | Chen |
| 2011/0070557 A1* | 3/2011 | Elyav ............... A61C 8/0018 433/174 |
| 2011/0294094 A1* | 12/2011 | Moshavi ............... A61C 8/0022 433/174 |
| 2012/0015325 A1 | 1/2012 | Chen |
| 2012/0225407 A1* | 9/2012 | Chen ............... A61C 8/0037 433/174 |
| 2013/0022942 A1* | 1/2013 | Zadeh ............... A61C 8/0024 433/174 |
| 2013/0045462 A1 | 2/2013 | Tzeng |
| 2013/0224687 A1 | 8/2013 | Karmon |
| 2013/0273500 A1 | 10/2013 | Giorno |
| 2014/0023990 A1 | 1/2014 | Zadeh |
| 2014/0045144 A1 | 2/2014 | Dukhan |
| 2015/0215696 A1* | 7/2015 | Bjorn ............... H04R 25/606 600/25 |

FOREIGN PATENT DOCUMENTS

| | | |
|---|---|---|
| CN | 103271774 | 9/2013 |
| DE | 10 2006 013 456 A1 | 9/2007 |
| EP | 1030622 A2 | 2/2006 |
| EP | 2095790 A2 | 9/2009 |
| EP | 2377490 A2 | 10/2011 |
| EP | 2377491 A2 | 10/2011 |
| EP | 2392289 A1 | 12/2011 |
| EP | 2656813 A1 | 10/2013 |
| RO | 110899 B1 | 5/1996 |
| WO | WO2010/108794 | 9/2010 |
| WO | WO 2013/157756 A1 | 10/2013 |
| WO | WO 2014/026706 A1 | 2/2014 |
| WO | WO 2015/118543 A1 | 8/2015 |
| WO | WO 2015/125139 A2 | 8/2015 |

* cited by examiner

DENTAL IMPLANT

BACKGROUND OF THE INVENTION

The present invention relates to a dental implant for preserving soft tissue health and aesthetics, promoting bone growth and bone augmentation. The invention further relates to an implant system and a method for implanting said implant.

STATE OF THE ART

An increasing share of patients is asking for an implant-supported tooth or an implant-supported denture instead of traditional prostheses. This is a result of the ongoing progress and improvements of dental implants as well as the methods needed to achieve an implantation that provides the desired biomechanical and biological properties at the implantation site. By now, dental implants are able to provide a long lasting solution not only in terms of function but also in terms of aesthetics.

The increasing demand for these dental replacements drives this field of technology to also develop new and better solutions for patients that may need a more advanced treatment to achieve the desired results. One of the most important factors for a favorable outcome of an implantation is bone quantity and quality that can be relied on for anchoring the implant.

The stability of an implant, which is fitted in a jaw bone hole created at least partly through tooth root extraction, is quite often insufficient due to the irregular geometry of the hole. WO 2004/010887 of Nobel Biocare® discloses a way of increasing the stability of an implant in a hole created by tooth root extraction.

One first approach relies on augmentation of the bone tissue using surgical techniques, wherein a second approach concentrates on adapting the design of the implant. For the latter, it is for example possible to change the dimensions of the features of an implant or the implant's surface in order to stimulate osseointegration. A successful example of a surface that demonstrated a positive effect on osseointegration is the TiUnite® surface developed and marketed by Nobel Biocare®.

Concerning bone augmentation, there are numerous techniques suggested by the prior art. These techniques are based on the introduction of graft material from different sources. Examples of graft materials used for augmenting are Autografts, Allografts, Xenografts and Alloplasts. It has been shown that these materials have in general a high survival rate once being implanted (see Jensen, O. T.; "Report of the Sinus Consensus Conference of 1996"; Int J Oral Maxillofac Implants. 1998; 13 Suppl:11-45. Review). However, Autografts require additional surgery, often inflicting pain for the patient and have a limited availability. With Allografts, Xenografts and Alloplasts there is always a residual risk associated with the body being exposed to exogenic material. Further, the long term results of most of these materials in terms of their potential in remodeling and adaptation of the bone tissue to external loads are not fully understood.

In addition, the implant can be made to carry growth stimulating substances that are known to stimulate the formation of bone tissue. However, additional substances may incur cost. Moreover, since they are directly in contact with blood, and actively initiate a cell and molecular response their clinical use is therefore subject to extensive regulations.

Thus, there is a need for an implant that based on the previously mentioned augmentation technique to increase bone mass also provides the option to reduce or eliminate the need for exogenic material. In this respect, U.S. Pat. No. 6,604,945 B1 discloses a method and apparatus for embedding an implant in a way that encourages bone tissue growth in and around the implant. This is intended to be achieved by a bone-fragment collecting drill. The collected bone fragments are packed into helical channels and through holes prior the installation of the implant in the implantation hole. The bone material used for augmentation is autologous and the collection of bone material still has to be performed during steps that precede the insertion of the implant.

Bone augmentation may also be desired to improve implant rehabilitation aesthetics. Augmentation of resorbed alveolar ridges or/and alveolar ridges with aberration or/and fresh tooth extraction sockets may be needed in order to support soft tissue contours. Hence, it is desired to develop an implant that is able to stimulate bone growth and without using autografts from a second surgical step.

U.S. Pat. No. 6,273,722 B1 discloses a dental implant having a body with a diameter that is press fit into a hole drilled into a patient's jaw bone, and having a helical groove machined into the body diameter to improve the rate of growth of bone tissue to securely lock the implant in position. A shallow height oppositely wound helical thread may be added to increase the holding force upon initial fitting of the implant. None the less, the implant of U.S. Pat. No. '722 is a press fit implant, i. e. an implantation hole with precise diameter has to be prepared. In contrast to U.S. Pat. No. '945, the bone tissue taken out to create said hole is completely lost.

SUMMARY OF THE INVENTION

An implant, an implant system as well as a method for implantation of said implant/implant system is defined in the hereto attached independent claims. Further embodiments also addressing the objectives listed above are stated in the dependent claims.

The implant provided by the invention is a dental implant for promoting bone growth. It comprises an elongated implant body having a coronal end portion and an apical end portion, at least one external thread, a flute arrangement having a depth. The flute arrangement is propagating with a greater lead than the at least one thread, and said flute arrangement is being capable of scraping and transferring bone debris opposite to the insertion direction of the implant during insertion and said flute arrangement having at least two helical flutes that spiral in the direction of said at least one external thread.

The helical flutes are propagating at least one turn around the implant body like serpentines. Like handrails following a spiral staircase the helical flute can be made such that the tangent line at any point makes a constant angle with a fixed line, said fixed line propagating along an axis in the longitudinal direction of the implant. Similarly the helical propagation can be made with some deviations to the mathematical definition of helical and it is acknowledged that the flute can propagate with at least one turn around the axis of the implant and with a lead that on average is greater than the lead of the thread/s of said implant.

While the implant according to the invention is screwed into the implantation site, the helical flute collects bone tissue that is cut off during insertion as bone debris. The bone debris is transported in the opposite direction of insertion to be deposited in the coronal periphery of the implant in order to promote bone augmentation and bone repair, i. e. the healing reaction taking place post-operative.

This space may be an implantation hole prepared prior to insertion of the implant by using different known techniques to prepare the site for implantation of a bone implant according to the invention. In cases where the implant is used in fresh tooth extraction sockets, the sockets may not be exactly shaped as to fit the shape of the implant because of wide root canals, and posterior extraction sites often reveal more than one root. Other issues to deal with in this regard are alveolar ridge aberrations.

Incorporating more than one helical flute in the design of the dental implant has the effect that cutting forces during insertion of the implant are basically symmetrical. This facilitates stable insertion of the implant along its longitudinal axis.

Advantageously, the helical flute has a greater depth than the average thread depth of the implant. Preferably, the depth of the flute is 40% to 200% greater than the average thread depth, more preferably 60% to 150% more deep than the average thread depth. The relation of average thread and flute depth has proven more important than expected in providing enough driving force during insertion so as to enable a sufficient cutting and transport of bone debris during insertion of the implant in the hole.

Preferably, the thread extends beyond the flute arrangement in the coronal direction. This will help to form a seal by close bone to implant contact at the coronal portion when the implant is in its intended position.

More preferably, the flute has a coronal flank and an apical flank, wherein the apical flank provides a cutting edge. Furthermore, an angle ($\alpha$) as measured in the longitudinal cross section of the implant between the apical flank of said flute and a normal to the longitudinal axis of said implant is between 0° and 5°, preferably between 1° and 3°. The cutting of bone debris and subsequent collection in and transfer via the flutes to allow discharge near the coronal part of the implant is enabled by an angle of the apical flank in said range.

More advantageously, the at least one flute comprising a flute base between the coronal flank and the apical flank of the flute arrangement, the flute base, as measured in the longitudinal cross section of the implant, preferably being inclined toward the longitudinal axis in the direction of the apical end.

Furthermore, the diameter of the implant is greater in the coronal region. Preferably, the increase of implant diameter continues from the apical section to the coronal section allowing for a steady contribution of bone debris to the respective flutes during insertion of said implant.

In one embodiment the implant includes a coronal section and an apical section, the coronal section and the apical section is separated by a knee, wherein at least the apical section, below said knee, is tapered toward the apical end portion.

More specifically, a preferred embodiment is designed so that the cone angle ($\gamma$) of the coronal section is less than the cone angle ($\delta$) of the apical section.

According to a preferred embodiment the external thread starts at the apical end portion and has its greatest height from the implant body at the knee. Furthermore, the extent of the thread flank may increase toward the coronal end. This will provide for additional bone contact of the implant threads and stability of the implant once positioned.

In this embodiment, the apical section as well as the coronal section generally has a frusta-conical shape. The apical section primarily provides bone debris, whereas the coronal section is adapted to increase the press fit between the dental implant and the surrounding bone tissue, in particular the cortical bone of the alveolar arch. More specifically, the cutting depth of the thread in the uppermost coronal section is less than in the apical section so that the increase in the implant's diameter tends to compress the surrounding bone tissue rather than to cut it off.

In a further embodiment, the width of the thread flank between one root to the next root may increase toward the coronal end. Thus, the coronal end of the implant located at the entry of the implantation hole provides a press fit that is not affected by the groove of the flute.

In yet another embodiment of the present invention, a self-tapping arrangement comprising a flute and a thread starts at the apical end and expands to its greatest height at the knee. Besides providing more bone debris due to the increasing height of the self-tapping arrangement. This also results in an increasing pulling force of the thread for enabling a press-fit and high primary implant stability during the initial healing phase.

In a further embodiment of the present invention, at least one of the flanks, the external thread and the flute comprises at least one groove. Such a groove/s have been shown to be advantageous for securing the implant in the bone tissue since it promotes bone growth, in particular for long term stabilization after healing when the effect of the press fit has decreased.

The invention also provides an implant system, comprising a dental implant according to this invention and prosthesis. Such an implant system provides the necessary tool for a professional to adapt the restoration technique of the prosthetic construction in order to individually respond to the needs of each patient. In accordance with various embodiments of the implant system, the prosthetic construction comprises at least one of an abutment, an abutment screw, a bridge, and a prosthetic tooth.

Further, the invention provides a method for implanting a dental implant according to the invention, comprising the following steps:

drilling an implantation hole;

placing the implant in the hole and screwing the implant during which screwing operation bone debris is transferred via at least one of said flutes to least partly fill a void space or/and augment the alveolar ridge, near the coronal portion of said implant, with bone debris.

Preparing the hole in such a way allows for cutting off bone debris immediately after starting screwing the implant in to the hole. Although additional tissue may be provided to the void space or/and the alveolar ridge, it is preferred to only use bone debris that has been transported by the flute of the implant into the space while being inserted into said implantation hole in order to fully use the advantages of autologous bone tissue.

A method in which a hole is a blind hole having a diameter at its entry that allows the tip of the implant to enter until an apical flank of the external thread touches the bone and screwing of the implant may begin.

In a further embodiment of the invention, the method comprises the step of placing any prosthesis on said implant. By placing the prosthesis on said implant, the treatment, probably after a defined healing period, is finalized.

DESCRIPTION OF THE DRAWINGS

In the following features that have similar characteristics or are directed to similar functions are designated with associated reference numbers.

DESCRIPTION OF PREFERRED EMBODIMENTS

Figure 1A:
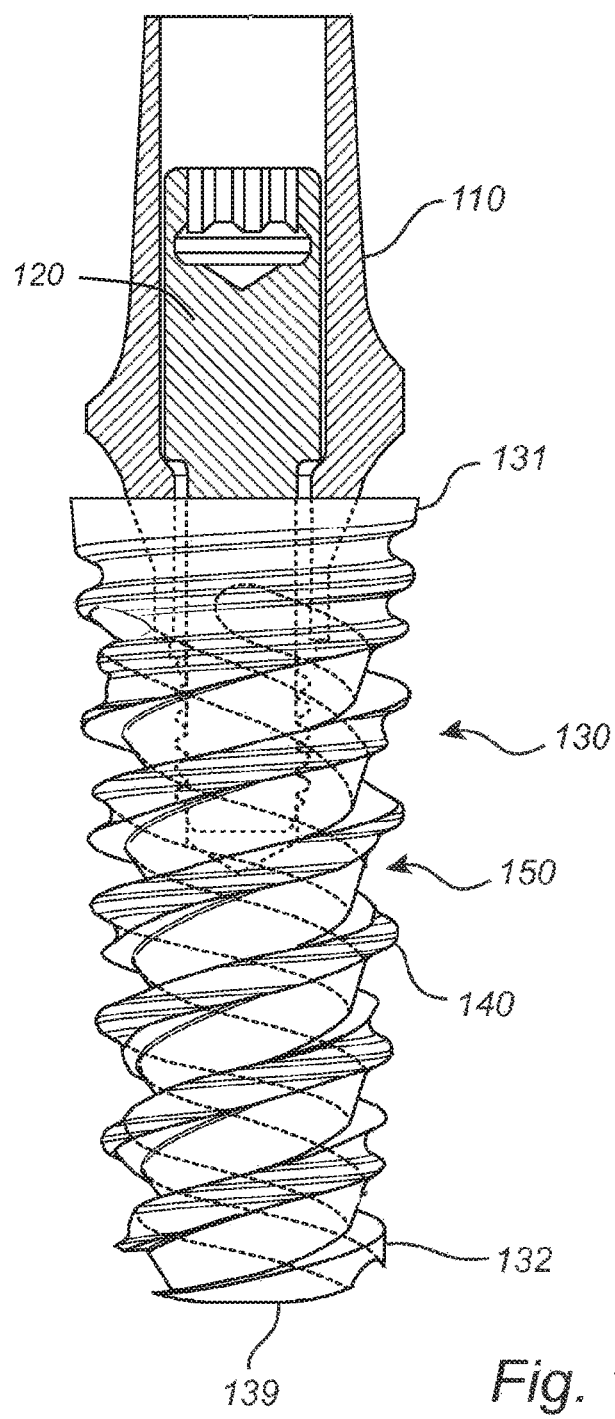
FIG. 1A is a side view of an implant system comprising a dental implant according to one embodiment of the invention.

FIG. 1A shows an implant system comprising an abutment 110, an abutment screw 120, and a dental implant 130 according to the invention. However, the abutment 110 and the abutment screw 120 may be replaced by any other prosthetic components of the art.

The dental implant 130 of FIG. 1A substantially has a frusta-conical shape. This general shape is merely one of the preferred general shapes of the invention as will be seen below. Corresponding features in other embodiments are given corresponding last two digits in the numbering system in the drawings. In order to facilitate reading the numbering used in the present drawing is used when describing a certain feature of an embodiment. It is realized that various combinations of features or embodiments, not disclosed in detail, can be made without departing from the scope of the present invention.

The body of the implant 130 comprises a coronal end 131 and an apical end 132. At the coronal end 131 there is an interface for mounting prosthetic components, such as an abutment 110 and an abutment screw 120. For, example an interface to a prosthetic component as defined in U.S. Pat. No. 6,733,291 B1, US 2011/0020767 A1, US 2012/0021381 A1, U.S. Pat. No. 8,038,442 B2 or U.S. Pat. No. 4,960,381 A may be included.

At the apical end 132, the implant 130 is provided with a flat tip 139.

The dental implant 130 is provided with an external thread 140, starting at the apical end 132 and spiraling along the outer side of the implant 130 toward the coronal end 131. The thread ends on the collar or just before the collar of the implant. The thread profile of the external thread 140 may change along the length of the implant 130. At the apical end 132 the thread profile may have a reduced thread depth compared to the thread profile at the coronal end 131. In between, the thread depths gradually increase. Such thread geometry is one way to provide the implant 130 with self-tapping property when a cutting feature such as the flute is added.

The thread 140 shown in FIG. 1A is a double thread. Alternatively, one, three or four threads may be provided along the outer side of dental implant 130. However, preferably, a double thread is used.

Two or more threads have an advantageous effect on the characteristics of the implant 130. More specifically, by using a plurality of threads 140 along the implant 130, the risk of misalignment while screwing in the implant 130 is significantly reduced. For example, the double thread 140 enters the bone tissue symmetrically so that even in the beginning of insertion, the center of rotation of the implant 130 is practically identical to the longitudinal axis 2 of the implant 130. Consequently, the likelihood of tilting of the implant 130 during insertion is reduced.

Further, two or more threads 140 also provide for a more evenly distributed loading of the bone tissue while tightening the implant 130. For the sake of simplicity, the term pitch is used in the following for the axial distance between two crests of a single thread and the term lead is used for the distance between two crests belonging to the same thread of a double thread. In other words lead is the distance the implant propagates during one full turn during insertion. For a single threaded implant the thread pitch and lead will be equal.

An implant according to the present invention is also provided with at least two helical cutting flutes 150 a, 150 b spiraling substantially in the direction of the external thread 140. As will be disclosed also in the embodiment of FIG. 2 the cutting flute 150 comprises a coronal flank 151, an apical flank 153 and a flute base 152 connecting the inner edges of the apical flank 153 and coronal flank 151. It will be appreciated that the profile of the cutting flute may be at least partly curved. Further, the flute base 152 may merge with either of the coronal flank 151 or the apical flank 153. In another embodiment, the coronal flank may directly connect to the apical flank at a point closest to the longitudinal axis 2. However, in all of these configurations, the apical flank 153 constitutes a cutting edge 154 and will act as a cutting flank.

Figure 2:
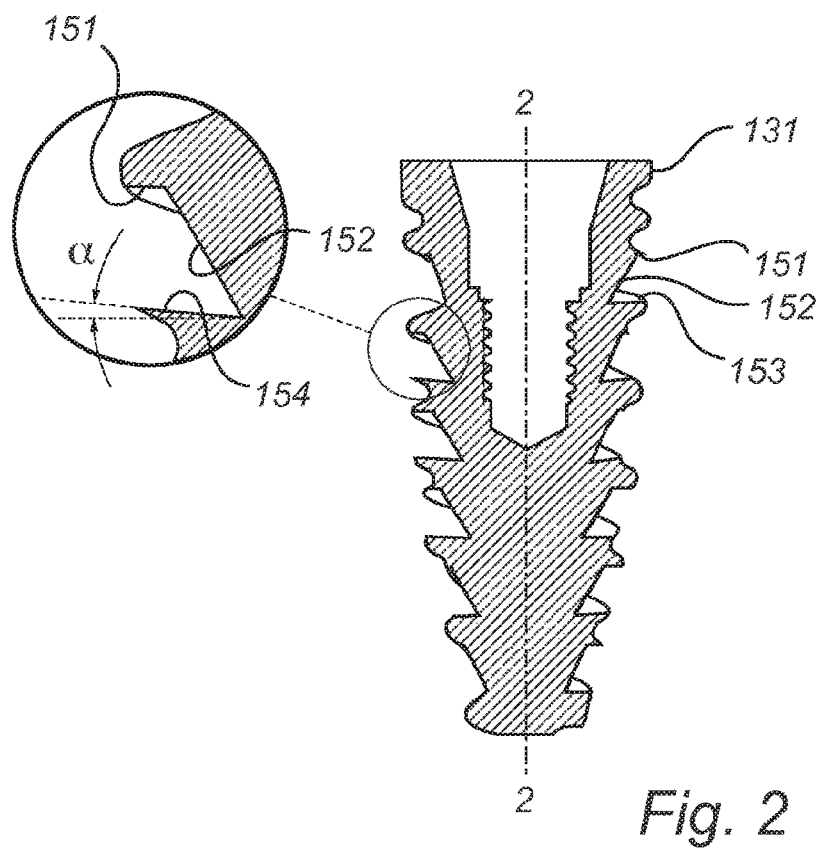
FIG. 2 is a cross-section of the implant system in the longitudinal direction along intersection line II-II of FIG. 1B.

Preferably, the apical flank 153 is longer than the coronal flank 53. As a result, the flute base 52 in FIG. 2 is not running parallel to the longitudinal axis 2 of said implant 130. Instead, the flute base 52 is inclined toward the central axis 2 in the direction of the apical end 132.

As can be seen in FIG. 1A, the cutting flutes helically runs from the apical end portion 132 along the outer side of implant 130 toward the coronal end 131 and preferably ends at a height so that at least one crest of thread 140 as seen in the longitudinal cross-section along the central axis 2 remains. However, preferably, two crests of thread 140 along the outer side of implant 130 remain in the coronal direction along central axis after tapering off of the helical flute 150. The tapering off of the helical flute is made in order to provide an easy exit of bone debris.

Further, the two helical flutes 150 preferably circumvents the implant 130 at least twice and at most the number of times of the at least one external thread 140. The preferred design of the flute results in a slightly steeper propagation of any flute than any thread of an embodiment according to the invention.

Although more than two flutes are achievable it has been found that an advantageous number of flutes, spiraling in the direction of the external thread(s) 140 and symmetrically distributed around the longitudinal axis, is two.

Referring to e.g. FIGS. 1A and 2 it is shown that the cutting flutes 150 spiral along the outer side of the implant in the direction of the external thread 140 but slightly steeper. Thus, the flutes 150 intersect the external thread 140. This intersection with the external thread 140 causes the apical flank 153 to form a cutting edge 154. Said cutting edge 154 enables the external thread 140 to provide a self-tapping function to the implant.

Since cutting is performed at the cutting edge 154 belonging to the apical flank 153, the apical flank 153 being longer than the coronal flank 151. The space provided to collect bone debris within said flute while the implant 130 is screwed into the bone is ideally made greater in giving the apical flank and bottom of the flute an ideal shape. In order to provide a cutting edge 154 that runs along the whole cross-section of the external thread geometry, the cutting flute 150 needs to have a greater depth than the external thread 140. Preferably, the flute has an at least 40% to 200% greater depth than the depth of the external thread 140. Consequently, the depth of the apical flank 153 has to be at least 40% deeper than the depth of thread 140.

There exist flutes in the prior art that commonly run along a portion of the implant in its longitudinal direction. Such flutes are and have been used to passively collect bone debris resulting from the screwing operation of the implant when its thread is in contact with the bone. The spiraling cutting flutes 150 in accordance with the present invention are designed to collect and discharge bone debris. The cutting flutes 150 spiraling along the implant also has the advantage, that the length of the cutting edge is increased in comparison to flutes known from the prior art. Such an increased length of the cutting edge provides for an even distribution of cutting forces and a more equal distribution of cut off bone tissue as well as its collection in the helical flute 150.

Figure 1B:
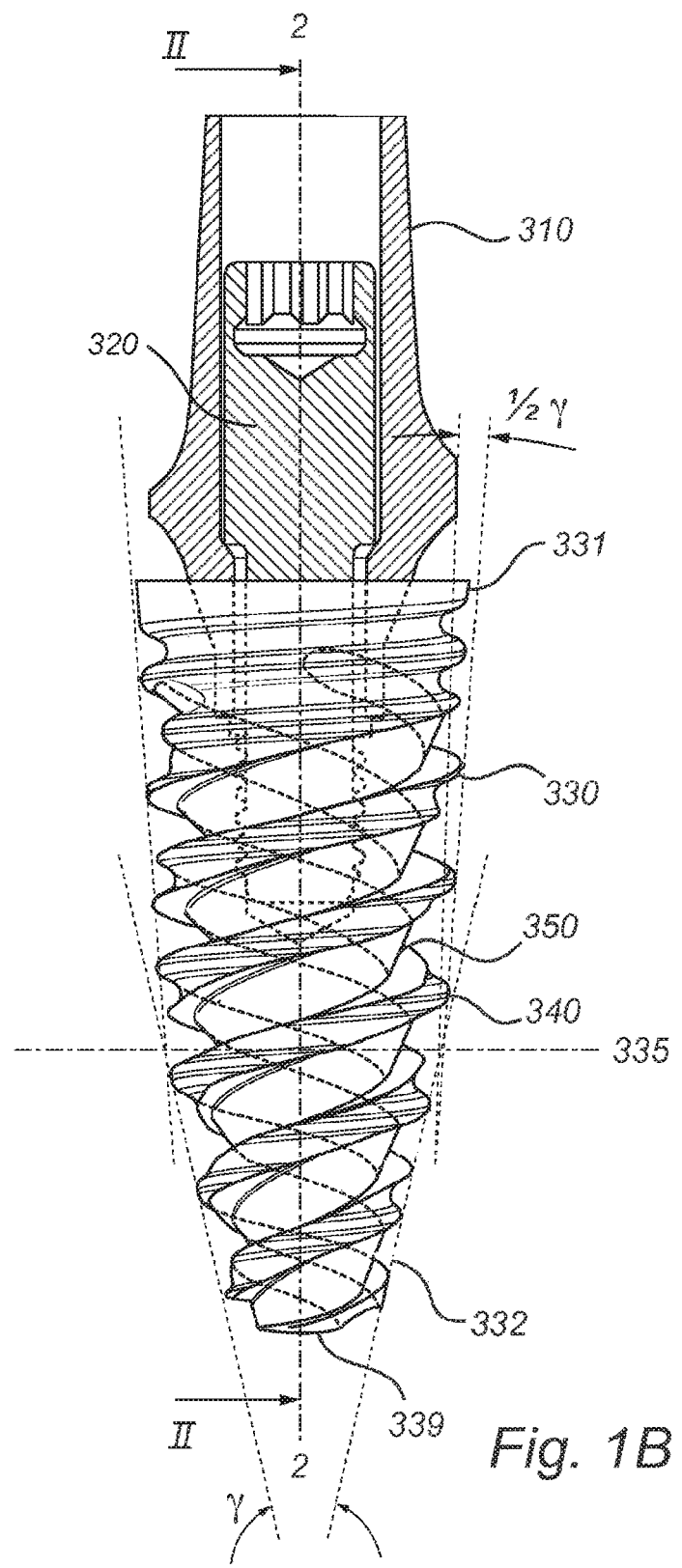
FIG. 1B is a side view of an implant system comprising a dental implant according to another embodiment of the present invention.

Preferably, and as seen in FIGS. 1A and 1B, the lead of the cutting flute 150, 350 is higher than the lead of the external thread 140, 340, respectively. Since the lead of the flute 150, 350 is higher than the lead of the external thread 140, 340, at least parts of the bone debris is transported a shorter distance, relative to the direction of insertion, than the implant 130 itself. More specifically, bone tissue is cut off by the cutting edge and is subsequently being positioned within the flute 150, 350. However, the cut off bone tissue is at least not fully attached to the cutting flute 150, 350 but, instead, will tend to move in the coronal direction of the implant 130, 330. Consequently, the bone debris will be transported toward the coronal end 131, 331 of said implant 130, 330 during insertion of the implant.

The hole prepared for implantation of an implant 130, 330 has at least a diameter that allows the implant 130, 330 to be inserted partly into the bone tissue until the surrounding rim of the implantation hole touches the apical flank of the thread 140, 340.

The implant 130 of FIG. 1A has a frusta-conical shape that is tapered toward its apical end 132. Such a shape makes it possible for the flutes to continuously cut off of bone tissue along the outer side of the implant 130. More specifically, the diameter of the implantation hole prepared prior to insertion of the implant is preferably chosen to be as small as possible allowing just about for the apical tip of the implant to enter. This allows the implant 130 to be inserted with its tip until the thread of the implant 130 contacts the circumferential rim of the implantation hole. In this way, the hole provides for an initial guidance of the implant into the implantation hole.

Subsequently, cutting of the bone tissue starts upon screwing the implant into the implantation hole. As will be appreciated, the conical form of the implant 130 results in the cutting edge not only cutting the thread geometry but at the same time increasing the diameter of the prefabricated implantation hole. Thus, the implant 130 may also act like a drill during implantation, in particular if the depth of the flute 150 is greater than the height of the external thread 140.

Since bone debris, resulting from expanding the hole as well as cutting the female thread in the bone, is collected in the flute 150, it will at least partly be moved toward the exit of the hole. In particular, the dental implant of the present invention may be used in patients, in which it is of advantage to use bone augmentation for providing support for soft tissue contours and an improved implant stability within the bone tissue.

Now referring to FIG. 1B, another embodiment of the implant similar to the one shown in FIG. 1A is disclosed. In this respect, features, advantages and effects previously described for the dental implant of FIG. 1A also apply to the implant of FIG. 1B. Further, features corresponding to features of the previous embodiment are denoted with associated reference numbers, i.e. the reference numbers have been changed by hundreds. This also applies to other embodiments described in the description.

The embodiment of the dental implant 330 shown in FIG. 1B comprises a coronal section 331 and an apical section 332. The coronal section 331 of the implant is frusta-conical but may also be cylindrical. On the other hand, the apical section 332 of the implant is designed to be frusta-conical in order to shave off and accumulate bone tissue in the form of bone debris when screwed into e.g. an under prepared hole. The bone debris is to be subsequently used for bone augmentation, preferably in the coronal periphery of implant 330. Between the coronal section 331 and the apical section 333, there is a knee 335 due to a difference in cone angles $\delta$ and $\gamma$ of the apical section 332 and the coronal section 331, respectively. As shown in FIG. 1B, the cone angle $\delta$ of the apical section 332 is greater than the cone angle $\gamma$ of the coronal section 331.

As a result, besides cutting the female thread into the surrounding bone tissue, the apical section 332 also serves to increase the diameter of the implantation hole. In contrast, the coronal section 331 is primarily intended for providing primary stability. In other words, the bone tissue is compressed in order to generate a press fit between the surface of the thread 340 and the surrounding bone tissue. This may be achieved by letting the flute 350 start to taper off after crossing the knee 335 in the coronal direction.

Preferably, the flute 350 extends beyond the knee up to the second last thread of the external thread 340 as seen in the longitudinal cross-section along the central axis 2.

Preferably, the final geometry of the external thread 340 is reached at the height of the knee 335. However, the width of a thread between a thread root and an adjacent thread root may well increase starting from the apical end 332 beyond the knee 335, even up to the coronal end 331. Such a design of the external thread 340 additionally provides primary stability of the implant. More details concerning the geometry of such a thread may be taken from e.g. NobelActive U.S. Pat. No. 8,038,442 B2 and US 2012/0021381.

FIG. 2 shows a longitudinal cross-section of implant along the line II-II shown in FIG. 1B. As depicted in the detail of FIG. 2, the apical flank with the cutting edge 154 is tilted by an angle $\alpha$ about the normal to the longitudinal axis 2 of the implant at the apical portion of the flute. Thus, bone tissue cut by the cutting edge 154 propagates in the direction of the flute basis 152 while bone is cut off from the circumferential wall of the implantation hole during insertion of the implant. Naturally, such a tilted apical flank 153 is also applied to any one of the other preferred embodiments of the invention, such as the one shown in FIG. 1A.

Figures 3A, 3B, 3C:
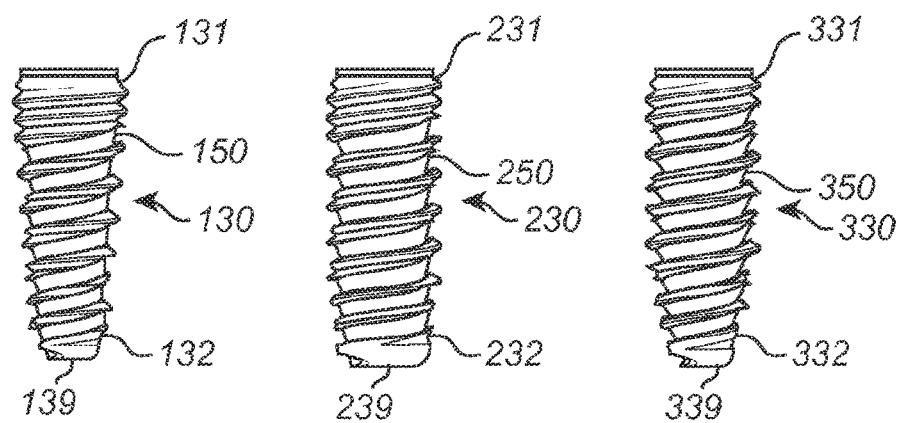
FIG. 3A is another side view of the first embodiment of the dental implant according to the invention.
FIG. 3B is a side view of a third embodiment of a dental implant according to the invention.
FIG. 3C is another side view of the second embodiment of a dental implant according to the invention.

FIGS. 3A to 3C show different shapes applied to the dental implant. The embodiment shown in FIG. 3A corresponds to the embodiment shown in FIG. 1A. In this embodiment, the coronal as well as the apical section has the same cone angle so that the whole implant 130 substantially has a frusta-conical shape. In contrast, implant 230 shown in FIG. 3B is designed to be basically cylindrical along its length. Further, the embodiment of FIG. 3C shows another side view of the implant 330 of FIG. 1B and FIG. 2.

In the following, a procedure for implantation of an implant according to the invention will be described in more detail.

Figure 4B:
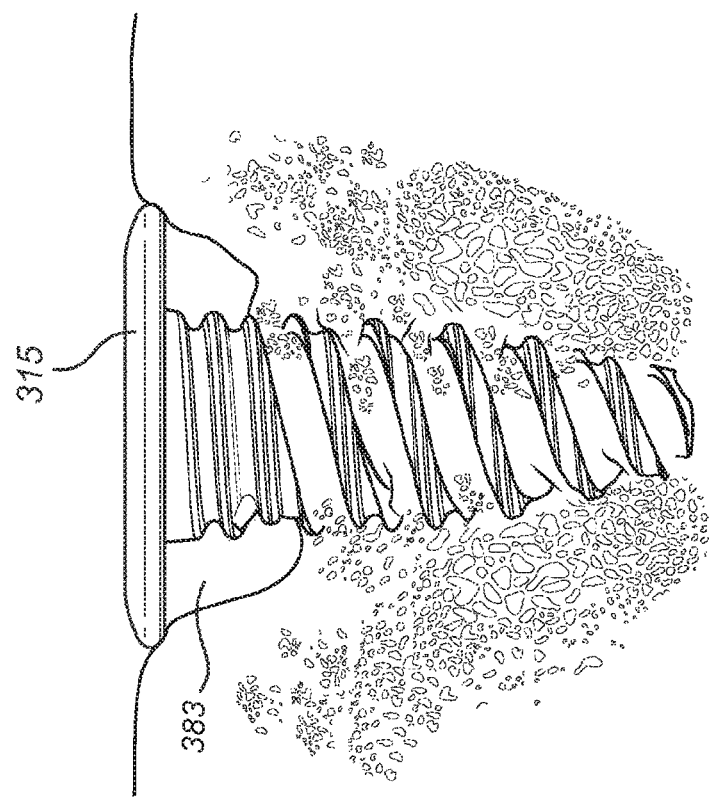
FIG. 4B is a perspective view of the implantation site showing the dental implant and a healing cap in its final position within the hole.
Figure 4A:
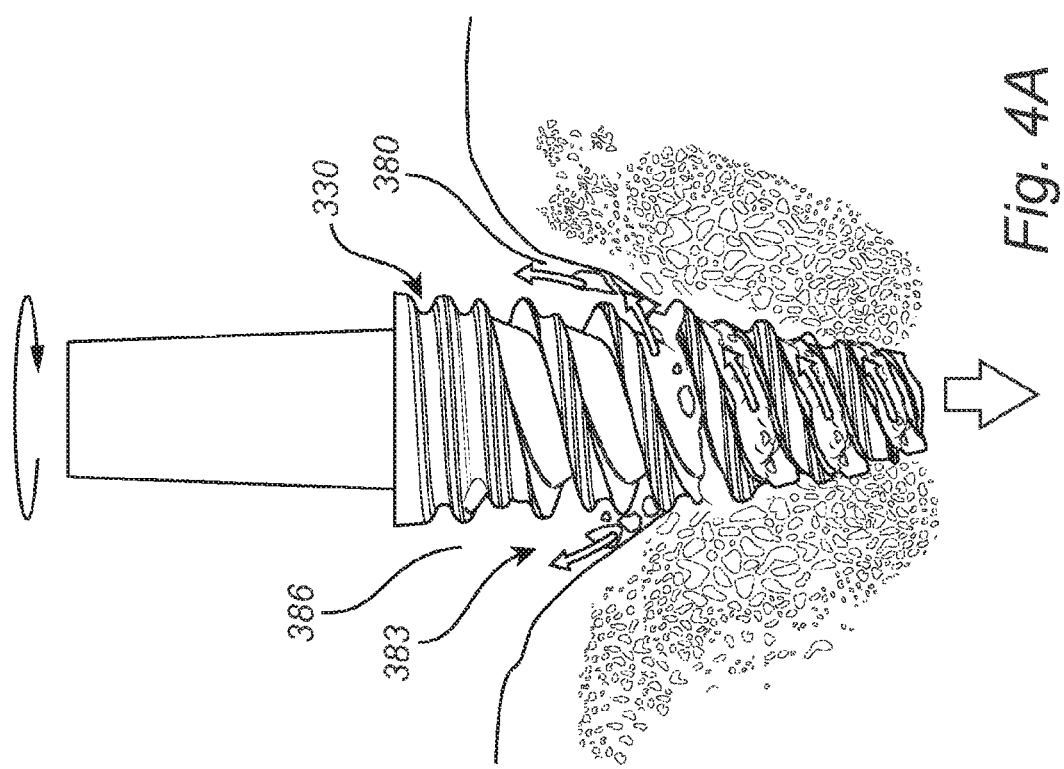
FIG. 4A is an enlarged perspective view of the implantation site showing the screwing action of a dental implant according to this invention.

In FIG. 4A, a drill has been used to drill the implantation hole 386. FIG. 4A shows the insertion of an implant 330 according to the present invention. Naturally, any of the other embodiments described above may be used instead. Since the implantation hole 386 is undersized compared to the diameter of implant 330, the coronal flank of the flute 350 cuts off bone debris 380 from the inner wall of implantation hole 386. As indicated by the arrow at reference sign 380, the bone debris 380 is urged along the helical flute towards the coronal end of implant 330 while said implant is screwed into the implantation hole 386. As can be seen, a void space 383 has been created and the bone debris on the sides of the hole 386 has been transported towards the coronal end of implant 330. The bone debris enters the void space 383 by exiting the flute, where the flute arrangement 350 exits or at the part of the flute extending into said space 383.

In FIG. 4B a following step of the procedure is shown, in which the accumulation of the bone debris stimulates bone augmentation in the space 383 between the hole walls and a cover screw 315.

Figure 4C:
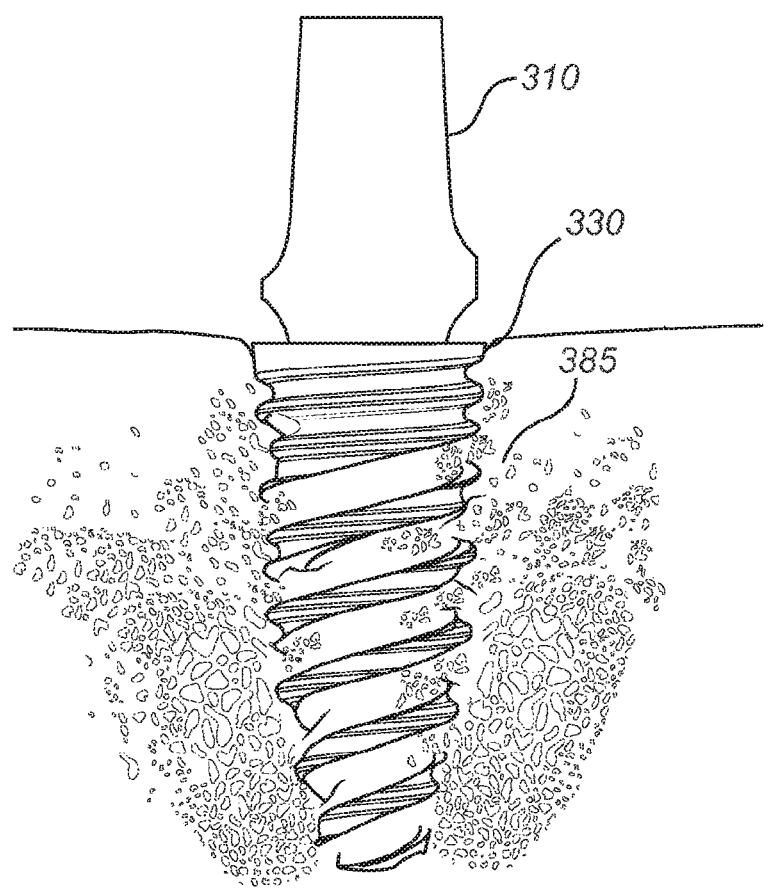
FIG. 4C is a perspective view of the implantation site after healing and installation of a dental prosthesis.

Once healed, prosthesis components 310 of any kind may be attached to the anchored implant 330 as disclosed in FIG. 4C. As can be seen at reference sign 385 in FIG. 4C, bone augmentation has successfully been achieved.

It will be understood by the skilled person that an implant according to the present invention may include at least one of a modified surface or a coating on at least part of its surface to enhance osseointegration. One example is the TiUnite® surface marketed by Nobel Biocare®.

It is furthermore realized that an implant system according to the claimed invention is suitable for use during quite extensive bone healing procedures including membranes and a plurality of implants such as disclosed in e.g U.S. Pat. No. 8,113,834. The purpose of growing bone to achieve suitable positions for the implants without the risk of reduced stability and/or compromised esthetics will be achieved using implants and methods in accordance with the disclosed invention. By using the bone chips from the patient a safe and reliable one-step procedure for bone augmentation is enabled.

As described above, the present invention provides a new generation of implant that may be applied in cases with insufficient bone quality or quantity. As will be understood by the person skilled in the art, the previous embodiments are intended for explanatory purposes only, whereas the scope of protection is defined by the following independent claims. Further combinations of features defining preferred embodiments are stated in the dependent claims.

The invention claimed is:

1. A dental implant for promoting bone growth, comprising:
   an elongated implant body having a coronal end portion and an apical end portion,
   at least one external thread having a thread depth,
   a flute arrangement having a depth,
   characterized in that said flute arrangement having at least two helical flutes that spiral in the general direction of said at least one external thread, that
   said at least two helical flutes having a greater depth than the thread depth and propagating with a greater lead than a lead of said at least one external thread, and
   said flute arrangement being capable of scraping off and transferring bone debris in the coronal direction of the implant during insertion,
       wherein the at least two helical flutes each has a coronal flank and an apical flank, wherein the apical flank provides a cutting edge, wherein the apical flank of at least one of the at least two helical flutes is tilted toward the coronal end portion by an angle about a normal to a longitudinal axis of the elongated implant body,
       wherein a flute base between the coronal flank and the apical flank of the flute arrangement, as measured in the longitudinal cross section of the implant, is inclined toward the longitudinal axis in the direction of the apical end.

2. The dental implant according to claim 1, wherein the greater depth of at least one of the at least two helical flutes is greater than the thread depth by 40% to 200%.

3. The dental implant according to claim 1, wherein the at least one external thread extends beyond the flute arrangement in a coronal direction.

4. The dental implant according to claim 1, wherein the angle is between 1° and 3°.

5. The dental implant according to claim 1, wherein a diameter of said implant is greater in a coronal region than in a more apical region.

6. The dental implant according to claim 1, wherein the implant includes a coronal section and an apical section, the coronal section and the apical section separated by a knee, wherein at least the apical section is tapered toward the apical end portion.

7. The dental implant according to claim 6, wherein a cone angle of the coronal section is less than a cone angle of the apical section.

8. The dental implant according to claim 6, wherein the at least one external thread starts at the apical end portion, and wherein the at least one external thread has its greatest height from the implant body at the knee.

9. The dental implant according to claim 1, wherein the width of the flank of the at least one external thread increases toward the coronal end.

10. The dental implant according to claim 1, wherein the implant comprises a prosthetic interface at the coronal end.

11. The dental implant according to claim 1, wherein at least one of the at least one external thread and the at least two helical flutes comprises at least one groove.

12. Implant system, comprising: a dental implant according to claim 1, and at least one prosthesis.

13. Implant system according to claim 12, wherein the prosthesis comprises at least one of an abutment, an abutment screw, a bridge, a bar and a prosthetic tooth.

14. A method for implanting a dental implant according to claim 1, comprising the steps:
   drilling an implantation hole;
   placing the implant in the hole and screwing the implant during which screwing operation bone debris is transferred via at least one of said flutes to at least partly fill a void space, near a coronal portion of said implant.

15. The method according to claim 14, wherein the hole is a blind hole having a diameter at an entry of the blind hole that allows an apical tip of the implant to enter until an apical flank of the at least one external thread touches the bone and screwing of the implant may begin.

16. The method according to claim 14, further comprising the step of placing a prosthesis on said implant.

* * * * *